United States Patent
Sackett

(10) Patent No.: US 10,012,603 B2
(45) Date of Patent: Jul. 3, 2018

(54) COMBINED HANDHELD XRF AND OES SYSTEMS AND METHODS

(71) Applicant: SciAps, Inc., Woburn, MA (US)

(72) Inventor: Donald W. Sackett, Bedford, MA (US)

(73) Assignee: SciAps, Inc., Woburn, MA (US)

(*) Notice: Subject to any disclaimer, the term of this patent is extended or adjusted under 35 U.S.C. 154(b) by 0 days.

(21) Appl. No.: 14/746,130

(22) Filed: Jun. 22, 2015

(65) Prior Publication Data

US 2015/0377805 A1 Dec. 31, 2015

Related U.S. Application Data

(60) Provisional application No. 62/016,901, filed on Jun. 25, 2014.

(51) Int. Cl.
*G01N 23/223* (2006.01)
*G01N 23/22* (2018.01)
(Continued)

(52) U.S. Cl.
CPC ......... *G01N 23/223* (2013.01); *G01N 21/718* (2013.01); *G01N 23/2208* (2013.01);
(Continued)

(58) Field of Classification Search
CPC .................. G01N 23/223; G01N 23/2076
See application file for complete search history.

(56) References Cited

U.S. PATENT DOCUMENTS 6,008,897 A 12/1999 Sabsabi et al.
6,320,388 B1 11/2001 Sun et al.
(Continued)

OTHER PUBLICATIONS

Written Opinion of the International Searching Authority; PCT Application No. PCT/US13/55706, dated Jan. 29, 2014 (ten (10) pages (unnumbered)).
(Continued)

*Primary Examiner* — David E Smith
*Assistant Examiner* — James Choi
(74) *Attorney, Agent, or Firm* — Tandiorio Teska & Coleman, LLP

(57) ABSTRACT

A combined handheld XRF and LIBS system and method includes an XRF subsystem with an X-ray source operated at a fixed medium voltage and configured to deliver X-rays to a sample without passing through a mechanized filter and a detector for detecting fluoresced radiation from the sample. The LIBS subsystem includes a low power laser source for delivering a laser beam to the sample and a narrow wavelength range spectrometer subsystem for analyzing optical emissions from the sample. The X-ray source is operated at the fixed medium voltage to analyze the sample for a first group of elements, namely, transition and/or heavy metals. The low power laser source is operated to analyze the sample for a second group of elements the XRF subsystem cannot reliably detect, namely, C, Be, Li, Na, and/or B, and to analyze the sample for a third group of elements the XRF subsystem cannot reliably detect at the fixed voltage, namely, Al, Si, and/or Mg, or where the XRF subsystem would require higher tube voltage, namely Cd, Ag, In, Sn, Sb, and/or Ba; and/or rare earth elements.

17 Claims, 2 Drawing Sheets

(51) Int. Cl.
  *G01N 21/71* (2006.01)
  *G01N 23/2208* (2018.01)
(52) U.S. Cl.
  CPC . *G01N 2223/045* (2013.01); *G01N 2223/076* (2013.01); *G01N 2223/402* (2013.01)

(56) References Cited

U.S. PATENT DOCUMENTS

| | | | |
|---|---|---|---|
| 6,512,810 B1 * | 1/2003 | Haszler | G01B 15/02 378/45 |
| 6,741,345 B2 | 5/2004 | Sabsabi et al. | |
| 6,753,957 B1 * | 6/2004 | Graft | G01N 21/718 356/318 |
| 6,762,835 B2 | 7/2004 | Zhang et al. | |
| 6,801,595 B2 * | 10/2004 | Grodzins | G01N 21/718 356/300 |
| 7,088,435 B2 | 8/2006 | Brestel et al. | |
| 7,233,643 B2 | 6/2007 | Sipila et al. | |
| 7,359,040 B1 | 4/2008 | Pendell-Jones et al. | |
| 7,430,273 B2 | 9/2008 | Yellepeddi | |
| 7,430,274 B2 | 9/2008 | Connors et al. | |
| 7,448,801 B2 | 11/2008 | Oettinger et al. | |
| 7,448,802 B2 | 11/2008 | Oettinger et al. | |
| 7,692,775 B2 | 4/2010 | Treado et al. | |
| 7,765,089 B2 | 7/2010 | Baxter | |
| 7,924,414 B2 | 4/2011 | Mound | |
| 7,945,393 B2 | 5/2011 | Treado et al. | |
| 7,999,928 B2 | 8/2011 | Beckstead et al. | |
| 8,112,248 B2 | 2/2012 | Schweitzer et al. | |
| 8,159,662 B2 | 4/2012 | Rezac et al. | |
| 8,355,126 B2 | 1/2013 | Goulter et al. | |
| 8,687,189 B2 | 4/2014 | Agarwal et al. | |
| 8,892,618 B2 | 11/2014 | Sun | |
| 2001/0034063 A1 | 10/2001 | Saunders et al. | |
| 2002/0093653 A1 | 7/2002 | Detalle et al. | |
| 2004/0051867 A1 | 3/2004 | Brestel et al. | |
| 2004/0189990 A1 | 9/2004 | Shilling | |
| 2006/0256330 A1 | 11/2006 | Leipertz et al. | |
| 2006/0262304 A1 | 11/2006 | Carron | |
| 2007/0153268 A1 | 7/2007 | Panza et al. | |
| 2007/0177130 A1 | 8/2007 | MacIntyre et al. | |
| 2007/0192035 A1 | 8/2007 | Schweitzer et al. | |
| 2008/0198365 A1 | 8/2008 | Treado et al. | |
| 2008/0268548 A1 | 10/2008 | Zuckerman | |
| 2008/0300826 A1 | 12/2008 | Schweitzer et al. | |
| 2009/0001262 A1 | 1/2009 | Visser et al. | |
| 2009/0012723 A1 | 1/2009 | Treado et al. | |
| 2009/0066947 A1 | 3/2009 | Bangalore et al. | |
| 2009/0101843 A1 | 4/2009 | Henshaw et al. | |
| 2009/0163369 A1 | 6/2009 | Treado et al. | |
| 2010/0171951 A1 | 7/2010 | Misra et al. | |
| 2010/0182594 A1 | 7/2010 | Carron | |
| 2011/0079734 A1 * | 4/2011 | Grodzins | G01N 21/63 250/461.1 |
| 2011/0080577 A1 | 4/2011 | Nelson et al. | |
| 2011/0237446 A1 | 9/2011 | Treado et al. | |
| 2012/0034686 A1 | 2/2012 | Berlin et al. | |
| 2012/0062697 A1 | 3/2012 | Treado et al. | |
| 2012/0062873 A1 | 3/2012 | Stewart et al. | |
| 2012/0065617 A1 | 3/2012 | Matsiev et al. | |
| 2012/0147358 A1 | 6/2012 | Gardner et al. | |
| 2013/0188181 A1 | 7/2013 | Angel et al. | |
| 2014/0204377 A1 | 7/2014 | Day et al. | |

OTHER PUBLICATIONS

Sharma et al., "Stand-off Raman spectroscopic detection of minerals on planetary surfaces", Spectrochimica Acts Part A 59 (2003), pp. 2391-2407.

* cited by examiner

COMBINED HANDHELD XRF AND OES SYSTEMS AND METHODS

RELATED APPLICATIONS

This application claims benefit of and priority to U.S. Provisional Application Ser. No. 62/016,901 filed Jun. 25, 2014 under 35 U.S.C. §§ 119, 120, 363, 365, and 37 C.F.R. § 1.55 and § 1.78 which is incorporated herein by this reference.

FIELD OF THE INVENTION

The subject invention relates to x-ray fluorescence (XRF) and optical emission spectroscopy (OES), for example, laser induced breakdown spectroscopy (LIBS) systems and methods.

BACKGROUND OF THE INVENTION

It has been proposed to combine an XRF analyzer with a LIBS or other optical emissions spectroscopy system in a portable handheld device. See, for example, U.S. Pat. Nos. 7,233,643; 6,801,595; and 7,430,273 all incorporated herein by this reference.

BRIEF SUMMARY OF THE INVENTION

The main idea of a combined system is that some elements in a sample are better detected by one type of spectroscopy. For example, LIBS is generally better at detecting and quantifying low atomic number elements such as Li, B, C, Be, Na that a portable XRF device cannot accurately measure. LIBS can also measure other low atomic number elements like Al, Mg and Si at lower concentrations and more precisely than a portable XRF device. Still, XRF is very good for measuring many transition and heavy metals, including Ni, Co, Cu, Zr, Nb, Mo, Ta, W. These elements can be more difficult to measure with LIBS, because many of these elements are very refractory and require a high laser energy to create a sufficiently good plasma. Such high energy lasers may not be commercially available in small enough form factors that can be powered by batteries, such as that needed for a handheld device. But, these elements can be measured with an x-ray tube device operating at a moderate voltage such as 30 kV.

But, XRF analyzers generally require a robust, fairly expensive x-ray tube capable of being driven at a low voltage (e.g., 10 kV) to detect some elements (e.g., aluminum, silicon, and/or magnesium) and driven a higher voltage levels (e.g., 30-50 kV) to detect other elements (e.g., the transition metals such as titanium, chromium, iron, nickel and copper, the heavy metals such as lead and gold, and transition metals that require high x-ray tube voltages (ideally 50 kV) including cadmium, silver, tin, and/or antimony). This method is often called a "multi beam operation".

Moreover, different beam filters are typically needed as between different power settings for the x-ray tube in order to optimally use the x-rays being emitted at a given power setting. For example, at a 10 kV setting, a thin (100 um or less) aluminum filter would be used or perhaps no filter at all. At a setting of 40 kV or 50 kV, a silver filter may be used to filter out the lower energy x-rays (less than about 20 keV). Thus, an XRF analyzer would require a filter wheel driven by a motor. See U.S. Pat. No. 7,430,274 incorporated herein by this reference.

Designing an XRF only analyzer with such an x-ray tube, a filter wheel, and a motor in a hand held device is difficult enough. Adding an OES (e.g., LIBS) analyzer with the required laser source, optics, and detector to all fit within a reasonably sized hand held housing would be extremely difficult. In addition, designing an XRF only analyzer as described above means the analyzer is larger and heavier, yet still does not offer the performance required for low atomic number elements.

Here, in this invention, in one preferred version, the large, robust x-ray tube, filter wheel, and motor are eliminated in the XRF subsystem to save space and a miniature x-ray tube is used instead and only operated at one mid-level power setting (e.g., a constant 30 kV) to analyze certain transition and heavy metals that would be difficult to analyze using a LIBS subsystem with a low power laser.

The OES (e.g., LIBS) analyzer section is then used to detect not only the elements that XRF cannot (e.g., carbon, beryllium, lithium, sodium, and boron) but also the elements the XRF section could detect at a lower power setting (which is not used here) (e.g., aluminum, silicon, and magnesium) and the elements the XRF section could detect at a higher power setting greater than 30 kV, for example (which is also not used here) (e.g., cadmium, silver, tin, antimony). In this way, the XRF and LIBS subsystems can be combined into a reasonably sized hand held analyzer.

The above combination also makes for a smaller, more compact OES spectrometer design as well. If only an OES technique is used, it is desirable to have both a wide wavelength range in the spectrometer and good resolution. A wide wavelength range is required if the OES technique is used to measure all the elements, in which case wavelengths ranging from about 170-180 nm up to 655-700 nm or more must be measured. Good resolution (e.g., 0.08-0.15 nm) is obtained by spreading the light from the spectrometer grating over as wide a range of sensors (typically four CCDs) as possible. In a portable analyzer, the resolution and range work in opposing directions. For a wider range, to preserve resolution, the spectrometer must grow proportionally in size.

An advantage of the combined technique presented above is that only certain elements need be measured by the OES technique. Therefore, specific optical lines can be selected so that the spectrometer subsystem can be small, cover a smaller wavelength range, and still maintain good resolution. Now, the LIBS subsystem need only cover a smaller wavelength range (e.g., 180 nm to 350 nm) while preserving or even improving the resolution. Moreover, this reduces the number of spectrometers (e.g., CCDs) required (e.g., from 4 to 2) thus reducing size and weight as well.

The subject invention, however, in other embodiments, need not achieve all these objectives and the claims hereof should not be limited to structures or methods capable of achieving these objectives.

Featured is a combined handheld XRF and LIBS system and method. The preferred XRF subsystem includes an X-ray source operated at a fixed medium voltage and configured to deliver X-rays to a sample without passing through a mechanized filter and a detector for detecting fluoresced radiation from the sample. The preferred LIBS subsystem includes a low power laser source for delivering a laser beam to the sample and a narrow wavelength range spectrometer subsystem for analyzing optical emissions from the sample. A controller subsystem is configured to operate the X-ray source at the fixed medium voltage to analyze the sample for a first group of elements, namely, transition and/or heavy metals and to process an output of the detector to determine the concentration of one or more elements of the first group in the sample. The controller also operates the low power laser source to analyze the sample for a second group of elements the XRF subsystem cannot reliably detect, namely, C, Be, Li, Na, and/or B. The controller also analyzes the sample for a third group of elements the XRF subsystem cannot reliably detect at the fixed voltage, namely, Al, Si, and/or Mg or where the XRF subsystem would require a higher tube voltage, namely Cd, Ag, In, Sn, Sb, Ba and/or the rare earth elements. The controller processes an output of the narrow wavelength range spectrometer subsystem to determine the concentration of one or more elements of the second and/or third groups in the sample.

In one example, the fixed medium voltage is less than or equal to approximately 30 Kv. The low power laser source may produce a 10 mJ/pulse and the narrow wavelength range is preferably 180-350 nm.

In one example, a combined handheld XRF and OES system includes an x-ray tube for delivering x-rays to a sample, a detector for detecting fluoresced radiation from the sample, a laser source for delivering a laser beam to the sample, and a spectrometer subsystem for analyzing optical emissions from the sample.

A controller subsystem is configured to operate the x-ray tube at a predetermined fixed power setting to analyze a first group of elements, process an output of the detector to determine the concentration of elements of the first group present in the sample, operate the laser source to analyze a second group of elements, and process an output of the spectrometer subsystem to determine the concentration of elements of the second group present in the sample.

The controller subsystem may be configured to operate the x-ray tube and laser source simultaneously and/or to energize the x-ray tube and the laser source for the same or approximate the same period of time.

The predetermined power setting may be between 20-40 kV and is preferably less than 30 kV. The first group of elements are elements the XRF subsystem detects and quantifies better than the LIBS subsystem such as transition metal and heavy metals. The second group of elements preferably includes elements an XRF subsystem cannot reliably detect and/or cannot reliably detect at the predetermined power setting such as C, Be, Li, Na; and/or B; Al, Si, and/or Mg; and/or Cd, Ag, In, Sn, Sb, Ba; and/or the rare earth elements.

Also featured is a method of analyzing a sample using both x-ray fluorescence and optical emissions spectrometry. One preferred method includes directing x-rays to a sample from an x-ray source operated at a predetermined power setting to analyze a first group of elements, detecting fluoresced radiation from the sample to detect the concentration of elements of the first group present in the sample, directing a laser beam to the sample to analyze a second group of elements, and analyzing emissions from the sample to detect the concentration of elements of the second group present in the sample.

BRIEF DESCRIPTION OF THE FIGURES

Other objects, features, and advantages will occur to those skilled in the art from the following description of a preferred embodiment and the accompanying drawings, in which.

DETAILED DESCRIPTION OF THE INVENTION

Figure 1:
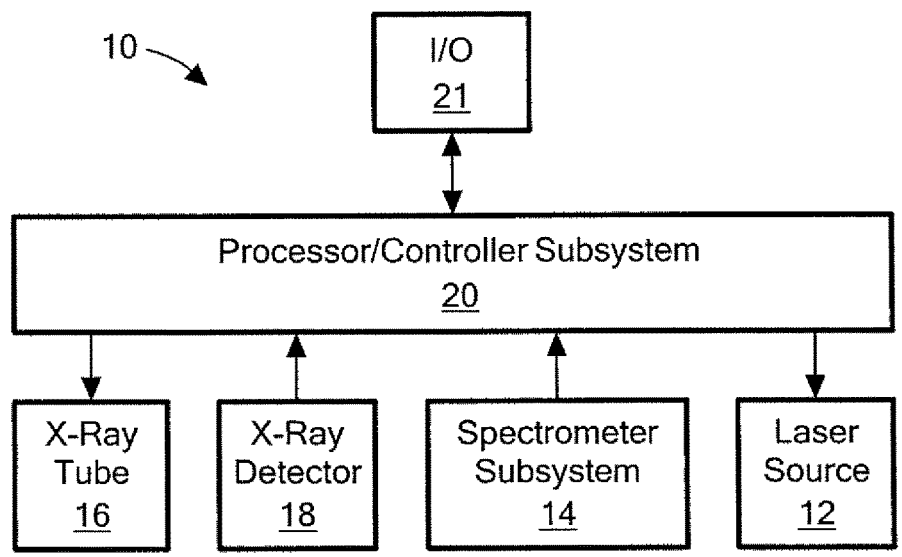
FIG. 1 is a block diagram showing several of the primary components associated with a combined XRF and OES handheld analyzer in accordance with the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Featured is a combined handheld XRF and DES system 10, FIG. 1 with a low power (e.g., 10 mJ/pulse) laser source 12 and a spectrometer subsystem 14 as the primary components of a LIBS analyzer subsystem which may configure as set forth in pending application Ser. No. 14/179,670 filed Feb. 13, 2014. The spectrometer subsystem may include one or more individual spectrometers. The spectrometer subsystem may be fairly small since the spectrometer subsystem need only be designed to cover a smaller wavelength range (e.g., 180 nm-350 nm). Thus, only one or two CCDs may be required.

The miniature x-ray tube 16 and x-ray detection subsystem 18 (typically including a silicon drift detector) are the primary components of the XRF analyzer subsystem. Preferably, the x-ray tube is a miniature tube as set forth in U.S. Pat. Nos. 7,448,801 and 7,448,802 incorporated herein by this reference. The x-ray tube may be a component of a module including a power supply.

Processor/controller subsystem 20 controls x-ray tube 16 to operate at a fixed voltage (typically between about 20 kV and 40 kV). In one example, a 30 kV setting is used. In some countries, the regulatory requirements concerning the use of x-ray tubes are relaxed somewhat if the x-ray tube is operated below 30 kV. So, advantageously, a setting of between 20 kV and 30 kV could be used. Operating the x-ray tube at 30 kV or less also makes the x-ray tube significantly smaller and lighter since less radiation shielding is required and less high-voltage insulation is required.

Preferably, no filter mechanisms are used or needed and the device is packaged in a handheld unit lacking a filter wheel or equivalent and its motor and associated controller(s).

Figure 2:
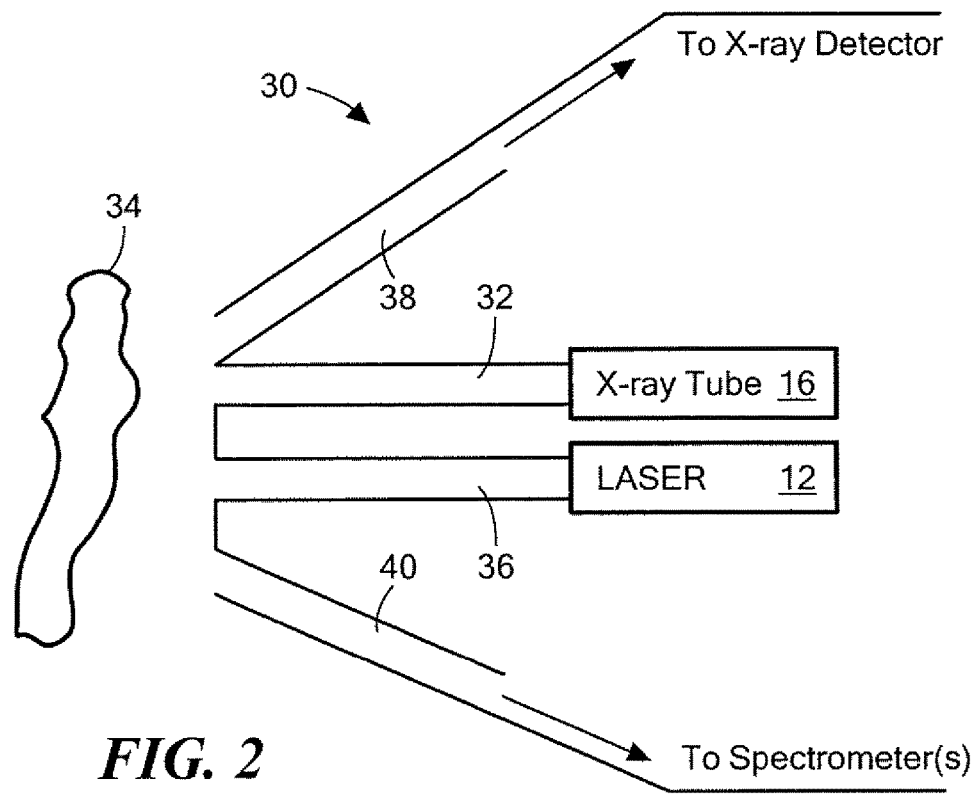
FIG. 2 is a schematic cross sectional view of the nose section of a handheld analyzer incorporating the components depicted in FIG. 1.

FIG. 2 shows nose 30 of a handheld unit with a channel 32 for delivering x-rays to sample 34, a channel 36 for directing laser energy to sample 34, channel 38 for delivering fluoresced energy to an x-ray detector, and channel 40 for delivering optical emissions to the spectrometer(s) of the device. The optical devices used in the various channels are not shown. Various mirrors, lenses, fiber optic devices and the like may be used.

Processor/controller subsystem 20, FIG. 1 controls the operation of x-ray tube 16 and laser source 12 and processes the outputs of x-ray detector 18 and spectrometer subsystem 14 to provide an output 21 to the user typically via a display at the rear of the handheld unit.

This processor/controller subsystem may be distributed and include one or more microcontrollers, driver circuitry, and the various power supply circuitry as well as digital signal processors, microprocessors, memories, and the like.

Figure 3:
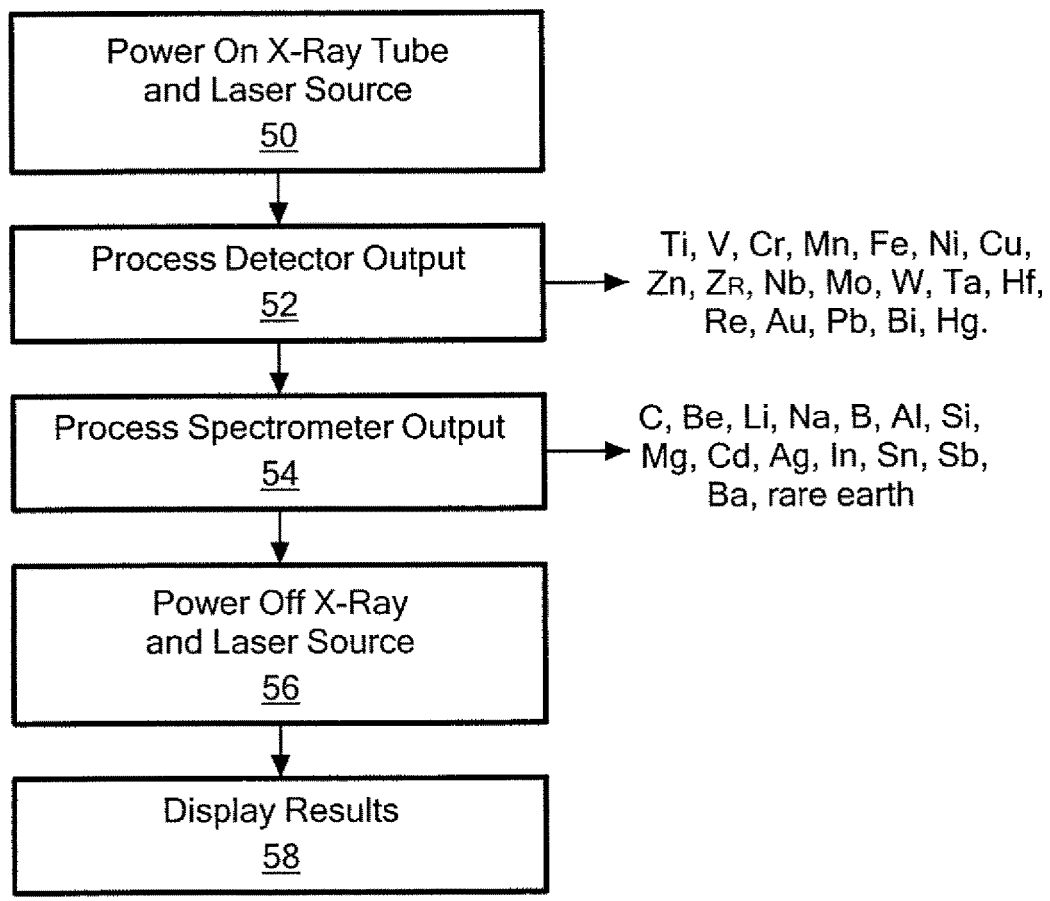
FIG. 3 is a flow chart depicting the primary steps associated with an exemplary method in accordance with the invention and also associated with the preferred programming of the processor/controller subsystem of FIG. 1.

In one example, subsystem 20 operates x-ray tube 16 and laser source 12 simultaneously, step 50, FIG. 3. In general, the XRF analyzer subsystem is used to analyze a first group of elements, step 52, for example many of the transition and heavy metals at a voltage setting of, for example, 29,000 volts to eliminate the need for a robust dual beam x-ray source and its complex power supply and driver circuitry requirements, and also to reduce the size and weight of the tube since it can operate at a fixed medium voltage, for example, 29,000 volts instead of 50,000 volts. Thus a much smaller x-ray tube is used. The transition metals analyzed by the x-ray tube are typically Ti, V, Cr, Mn, Fe, Ni, Cu, Zn, Zr, Nb and Mo (Ti through Mo). Heavy metals typically include W, Ta, Hf, Re, Au, Pb, Bi and Hg or more generally Hf through Bi. Thus, the XRF subsystem is used to reliably detect and quantify elements which can be more difficult to detect using a LIBS system. And, preferably, a mechanized filter (e.g., a filter wheel) is not required thus rendering the handheld device smaller, simpler in design, and less expensive.

The LIBS analyzer subsystem, in turn, is used as shown at step 54 to detect and determine the concentration of a second group elements, namely, elements the XRF subsystem cannot reliably detect (e.g., C, Be, Li, Na, and/or B), and the concentration of a third group of the elements which would require a lower x-ray tube voltage setting (e.g., Al, Si, and/or Mg), and the elements that would require a higher x-ray tube voltage setting (e.g., Cd, Ag, In, Sn, Sb, and/or Ba, and/or the rare elements (with atomic numbers 57-71)).

Thus, here, the number of elements detected and reported by the XRF analyzer subsystem is reduced (compared to commercially available portable XRF analyzers). XRF is used to detect elements that the XRF subsystem can reliably detect at a fixed medium voltage and which are easier to measure quantitatively with XRF than with a LIBS analysis. The LIBS subsystem, in turn is optimally used to detect and quantify elements the XRF analyzer operated at the fixed medium voltage cannot reliably detect and/or quantify.

This result renders the LIBS and XRF subsystems less complex allowing sufficient real estate for a combined system in a reasonably sized handheld device.

In step 56, the x-ray tube and laser source are powered off (typically simultaneously) and the results are stored and displayed to the user, step 58. Note too that unlike the method or U.S. Pat. No. 6,801,595, the results obtained by the XRF section and LIBS section stand alone and are not dependent on each other. Each section detects and reports the absolute concentration of certain elements.

In the configuration described, the two subsystems can be operated simultaneously. Also, due to recent advances in XRF measurement technology, namely the widespread use of silicon drift detectors (SDDs) in portable XRF analyzers, the XRF measurement time may often be faster than the OES measurement time.

Although specific features of the invention are shown in some drawings and not in others, however, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A combined handheld XRF and LIBS system comprising in a single housing:
    an XRF subsystem including:
        an X-ray source operated at a fixed medium voltage and configured to deliver X-rays to a sample without passing through a mechanized filter, and
        a detector for detecting fluoresced radiation from the sample;
    a LIBS subsystem including:
        a low power laser source for delivering a laser beam to the sample, and
        a narrow wavelength spectrometer subsystem for analyzing optical emissions from the sample; and
    a controller subsystem configured to:
        operate the X-ray source at the fixed medium voltage to analyze the sample for a first group of elements, namely, transition and/or heavy metals,
        process an output of the detector to determine the concentration of one or more elements of the first group in the sample, and
        operate the low power laser source to:
            analyze the sample for a second group of elements the XRF subsystem cannot reliably detect, namely, C, Be, Li, Na, and/or B,
            analyze the sample for a third group of elements the XRF subsystem cannot reliably detect at the fixed voltage, namely, Al, Si, and/or Mg and/or where the XRF subsystem would require higher tube voltage, namely Cd, Ag, In, Sn, Sb, and/or Ba and/or rare earth elements, and
            process an output of the narrow wavelength range spectrometer subsystem to determine the concentration of one or more elements of the second and/or third groups in the sample, wherein the first, second, and third groups of elements do not have any elements in common.

2. The system of claim 1 in which the fixed medium voltage is less than or equal to approximately 30 kV.

3. The system of claim 1 in which the low power laser source produces 10mJ/pulse.

4. The system of claim 1 in which the narrow wavelength spectrometer subsystem has a wavelength range of between 180-350 nm.

5. A method of analyzing a sample using both XRF and LIBS subsystems included in a single housing, the method comprising:
    operating an X-ray source at a fixed medium voltage to deliver X-rays to a sample without passing through a mechanized filter to analyze the sample for a first group of elements, namely, transition and/or heavy metals,
detecting fluoresced X-rays from the sample in a detector;
processing an output of the detector to determine the concentration of one or more elements of the first group in the sample;
employing a low power laser source to deliver a laser beam to the sample to analyze the sample for a second group of elements, namely, C, Be, Li, Na, and/or B and to analyze the sample for a third group of elements, namely, Al, Si, Mg, Cd, Ag, In, Sn, Sb, and/or Ba, and/or rare earth elements;
analyzing optical emissions from the sample using a narrow wavelength spectrometer subsystem; and
processing an output of the narrow wavelength spectrometer subsystem to determine the concentration of one or more elements of the second and/or third groups in the sample, wherein the first, second, and third groups of elements do not have any elements in common.

6. The method of claim 5 in which the fixed medium voltage is less than or equal to 30 kV.

7. The method of claim 5 in which the low power laser source produces 10mJ/pulse.

8. The method of claim 5 in which the narrow wavelength range is 180-350 nm.

9. A combined handheld XRF and OES system comprising in a single housing:
an x-ray tube for delivering x-rays to a sample;
a detector for detecting fluoresced radiation from the sample;
a laser source for delivering a laser beam to the sample;
a narrow wavelength spectrometer subsystem for analyzing optical emissions from the sample; and
a controller subsystem configured to:
 operate the x-ray tube at a predetermined fixed power setting to analyze a first group of elements,
 process an output of the detector to determine the concentration of elements of the first group present in the sample,
 operate the laser source to analyze a second group of elements, and
 process an output of the narrow wavelength spectrometer subsystem to determine the concentration of elements of the second group present in the sample, wherein the first and second groups of elements do not have any elements in common.

10. The system of claim 9 in which the controller subsystem is configured to operate the x-ray tube and laser source simultaneously.

11. The system of claim 10 in which the controller subsystem is configured to energize the x-ray tube and the laser source for the same or approximate the same period of time.

12. The system of claim 9 in which the predetermined power setting is between 20-40 kV.

13. The system of claim 9 in which the predetermined power setting is less than 30 kV.

14. The system of claim 9 in which the first group of elements include the transition metals and the heavy metals.

15. The system of claim 9 in which the second group of elements includes elements an-XRF subsystem cannot reliably detect.

16. The system of claim 15 in which the second group of elements further includes elements the XRF subsystem cannot reliably detect at said predetermined power setting.

17. The system of claim 16 in which the second group of elements include C, Be, Li, Na, and/or B; Al, Si, and/or Mg; and/or Cd, Ag, In, Sn, Sb, and/or Ba; and/or the rare earth elements.

* * * * *